United States Patent
Greiner (10) Patent No.: US 11,355,232 B2
(45) Date of Patent: Jun. 7, 2022

(54) AUTOMATED PERSONNEL IDENTIFICATION AND LOCATION, AND AUTOMATED PROCEDURE MONITORING

(71) Applicant: KONINKLIJKE PHILIPS N.V., Eindhoven (NL)

(72) Inventor: Harald Greiner, Nufringen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 259 days.

(21) Appl. No.: 16/084,580

(22) PCT Filed: Mar. 29, 2017

(86) PCT No.: PCT/EP2017/057354
§ 371 (c)(1),
(2) Date: Sep. 13, 2018

(87) PCT Pub. No.: WO2017/167775
PCT Pub. Date: Oct. 5, 2017

(65) Prior Publication Data
US 2019/0080796 A1 Mar. 14, 2019

(30) Foreign Application Priority Data
Mar. 30, 2016 (EP) ..................................... 16162981

(51) Int. Cl.
*G16H 40/20* (2018.01)
*G16H 30/20* (2018.01)
*A61B 5/00* (2006.01)

(52) U.S. Cl.
CPC ............. *G16H 40/20* (2018.01); *A61B 5/743* (2013.01); *A61B 5/7405* (2013.01); *G16H 30/20* (2018.01)

(58) Field of Classification Search
CPC ...... G16H 40/20; G16H 30/20; A61B 5/7405; A61B 5/743
USPC ............................................................ 705/2
See application file for complete search history.

(56) References Cited

U.S. PATENT DOCUMENTS

| 5,561,412 A | 10/1996 | Novak | |
| 8,425,415 B2 * | 4/2013 | Tran .................... | A61B 5/4833 600/300 |
| 10,004,447 B2 * | 6/2018 | Shen ..................... | A61G 7/057 |
| 2009/0091458 A1 | 4/2009 | Deutsch | |

(Continued)

FOREIGN PATENT DOCUMENTS

| JP | 2003099350 A | 4/2003 |
| JP | 2009211238 A | 9/2009 |

*Primary Examiner* — Michael Tomaszewski
*Assistant Examiner* — Rachael Sojin Stone (57) ABSTRACT

In accordance with some embodiments, the present disclosure relates to a method comprising: activating (200) one or more electronic devices (102) when the medical personnel enters a patient room; obtaining (202) image data acquired by the one or more electronic devices that captures the medical personnel; analyzing (204) the acquired image data to identify the medical personnel and at least one medical apparatus to be used by the medical personnel for the procedure; analyzing (212) the acquired image data to monitor the medical personnel's performance of the procedure using the at least one identified medical apparatus; and storing (214) data acquired from the monitored performance of the procedure in a database.

20 Claims, 6 Drawing Sheets (56) References Cited

U.S. PATENT DOCUMENTS

| | | | |
|---|---|---|---|
| 2010/0152600 A1* | 6/2010 | Droitcour | A61B 5/1114 600/534 |
| 2011/0276338 A1* | 11/2011 | Warner | G16H 40/20 705/2 |
| 2012/0075464 A1* | 3/2012 | Derenne | A61B 5/1113 348/135 |
| 2012/0212582 A1 | 8/2012 | Deutsch | |
| 2013/0103416 A1 | 4/2013 | Amigo | |
| 2013/0332184 A1 | 12/2013 | Burnham | |
| 2014/0002624 A1* | 1/2014 | Nemoto | A61B 1/00039 348/65 |
| 2014/0266709 A1 | 9/2014 | Nagase | |
| 2015/0018622 A1* | 1/2015 | Tesar | A61B 50/13 600/202 |
| 2015/0109442 A1 | 4/2015 | Derenne | |
| 2015/0209510 A1 | 7/2015 | Burkholz | |
| 2015/0282749 A1* | 10/2015 | Zand | A61B 1/0676 600/301 |
| 2015/0286799 A1* | 10/2015 | Padmani | G16H 20/10 705/3 |
| 2015/0324522 A1* | 11/2015 | Chan | G06F 16/24575 705/3 |
| 2018/0011982 A1* | 1/2018 | Hung | G06K 9/2018 |
| 2018/0357886 A1* | 12/2018 | Tavori | G16H 40/67 |
| 2018/0360543 A1* | 12/2018 | Roh | G16H 50/20 |
| 2019/0065763 A1* | 2/2019 | Berg | G06F 16/9566 |

\* cited by examiner

AUTOMATED PERSONNEL IDENTIFICATION AND LOCATION, AND AUTOMATED PROCEDURE MONITORING

CROSS REFERENCE TO RELATED APPLICATIONS

This application is the U.S. National Phase application under 35 U.S.C. § 371 of International Application No. PCT/EP2017/057354, filed Mar. 29, 2017, published as WO 2017/167775 on Oct. 5, 2017, which claims the benefit of European Patent Application Number 16162981.1 filed Mar. 30, 2016. These applications are hereby incorporated by reference herein.

BACKGROUND OF THE INVENTION

Hospitals may install various types of imaging systems for monitoring purposes. For example, automated image processing techniques may be used to track a patient's movements inside a patient room. The imaging systems may allow for enhanced security and/or provide for more responsive care, and they can be used with minimal disruption to the hospital's operation or environment.

Aside from monitoring the patient, automated monitoring of events such as medical and safety-related procedures inside a patient room can further enhance the quality of patient care. Specifically, automated monitoring can be used to ensure consistent compliance and monitoring of the required and scheduled medical procedures without having to rely on one or more hospital personnel to perform those monitoring constantly.

Imaging devices such as closed circuit televisions ("CCTVs") are widely used for all types of monitoring including hospital patient and personnel monitoring. However, many of these monitoring systems are not automated and still require human intervention to review the video feeds to conduct the monitoring of patients and medical personnel.

U.S. Pat. App. No. 2013/0332184 discloses a monitoring system for reducing the incidence of healthcare-associated infections. The monitoring system comprises sensors (e.g., hand sanitizer usage sensors) installed at strategic locations to detect and track compliance with infection reduction protocols such as those for pre- and post-surgical hygiene or cleansing protocols. U.S. Pat. App. No. 2013/0103416 discloses an activity evaluation system comprising video cameras or motion detectors. The activity evaluation system detects a patient's movement and activity that may be used for monitoring the patient's recovery or rehabilitation progress after suffering from a physical injury (e.g., broken limb).

SUMMARY OF THE INVENTION

The present disclosure relates to systems and methods for identifying, locating, and monitoring procedures performed by medical personnel.

In accordance with some embodiments, the present disclosure relates to a method comprising: activating one or more electronic devices when the medical personnel enters a patient room; obtaining image data acquired by the one or more electronic devices that captures the medical personnel; analyzing the acquired image data to identify the medical personnel and at least one medical apparatus to be used by the medical personnel for the procedure; analyzing the acquired image data to monitor the medical personnel's performance of the procedure using the at least one identified medical apparatus; and storing data acquired from the monitored performance of the procedure in a database.

In various embodiments, the acquired image data may be analyzed to monitor the medical personnel's performance of the procedure using the at least one identified medical apparatus to determine compliance with a protocol.

In various embodiments, the identification of the medical personnel may be based on a visual identification pattern uniquely assigned to the medical personnel. In various versions, the visual identification pattern may be generated by one or more infrared light sources. In various versions, the visual identification pattern may include printed indicia adorned by the medical personnel.

In various embodiments, analyzing the acquired image data to monitor the medical personnel's performance may include comparing one or more aspects of the acquired image data to one or more rules in a rules database. In various embodiments, the method may further include generating and rendering, using a speaker, audio output that notifies the medical personnel of non-compliance with the one or more rules.

In various embodiments, the method may further include acquiring, from the one or more electronic devices, audio data; and analyzing the acquired audio data to further identify the medical personnel. In various embodiments, the method may further include causing one or more light sources to emit a visual indication pattern that is associated with an identity of the medical personal. In various versions, the method may further include: obtaining location image data acquired by the one or more electronic devices that captures the one or more light sources emitting the visual indication pattern; determining, based on the location image data or a known location associated with the one or more light sources, a location of the medical personnel; and causing the determined location to be stored in a personnel location database. In various embodiments, the method may further include: obtaining audio data acquired by the one or more electronic devices that captures a spoken request for a location of a sought-after medical personnel; analyzing, using speech recognition, the audio data to identify the sought-after medical personnel; determining, based on data stored in the medical personnel location database, a last known location of the sought-after medical personnel; and generating audio output that includes an indication of the last known location of the sought-after medical personnel.

In accordance with some embodiments, the present disclosure relates to a system comprising: one or more light sources placed adjacent a patient's room to generate a visual identification pattern assigned to the medical personnel on determination that the medical personnel has entered the patient's room; one or more cameras to acquire image data that captures the visual identification pattern; logic to analyze the acquired image data to determine an identity of the medical personnel based on the captured visual identification pattern; and a database for storing a record of a location of the medical personal.

In various embodiments, the system may further comprise one or more processors to activate the one or more cameras when a medical personnel enters a patient room and to obtain image data acquired by the one or more cameras that captures the medical personnel.

In various embodiments, the logic may determine the location based on one or attributes of the camera that acquired the image data. In various embodiments, the logic may determine the location based on a known location of the one or more light sources. In various embodiments, the logic may determine the location of the medical personnel based on information modulated into the visual identification pattern. In various embodiments, the one or more cameras may comprise a first camera, the system may further comprise a rules database and a second camera to acquire image data that captures performance of a procedure by the medical personnel, and the logic may analyze the acquired image data that captures performance of the procedure to determine whether the medical personnel complied with one or more rules in the rules database.

BRIEF DESCRIPTION OF THE DRAWINGS

The accompanying drawings, which are included to provide a further understanding of the disclosure, are incorporated herein to illustrate embodiments of the disclosure. Along with the description, they also serve to explain the principle of the disclosure. In the drawings.

DETAILED DESCRIPTION

The following are definitions of terms as used in the various embodiments of the present disclosure.

The term "database" as used herein refers to a collection of data and information organized in such a way as to allow the data and information to be stored, retrieved, updated, and manipulated and to allow them to be presented into one or more formats such as in table form or to be grouped into text, numbers, images, and audio data. The term "database" as used herein may also refer to a portion of a larger database, which in this case forms a type of database within a database. "Database" as used herein also refers to conventional databases that may reside locally or that may be accessed from a remote location, e.g., remote network servers. The database typically resides in computer memory that includes various types of volatile and non-volatile computer memory. Memory that stores the database may include high-speed random access memory or non-volatile memory such as magnetic disk storage devices, optical storage devices, and flash memory. Memory that stores the database resides may also store one or more software for processing and organizing data received by and stored into the database.

The term "medical apparatus" as used herein refers to any device, instrument, equipment, or apparatus capable of measuring a physiological parameter, assisting in the diagnosis, or treating a physiological condition or disease. Examples of medical apparatus include but are not limited to X-ray machines, stethoscopes, radioactive spectrometers, blood pressure measurement devices, temperature measurement devices, dialysis machines, adjustable hospital beds, ultrasound equipment, magnetic resonance imaging ("MRI") equipment, physical therapy equipment, computerized tomography ("CT") equipment, infusion pumps, defibrillators, catheters, injection pens, and so forth. The term "electronic device" as used herein refers to any device capable of capturing, recording, or storing an image, video, and other forms of digital or electronic representation of an object or a scene. "Image data" as used herein refers to lossy data (e.g., JPEG) or lossless data (e.g., bitmap) representing one or more images acquired by an electronic device such as a camera. "Image data" may refer to a single image and/or to a sequence of images (e.g., a video). "Video data" as used herein may refer to a sequence of images.

The present disclosure relates to a system comprising: one or more light sources placed adjacent a patient's room to generate a visual identification pattern assigned to the medical personnel on determination that the medical personnel has entered the patient's room; one or more cameras to acquire image data that captures the visual identification pattern; logic to analyze the acquired image data to determine an identity of the medical personnel based on the captured visual identification pattern; and a database for storing a record of a location of the medical personal.

The present disclosure also relates to a method comprising: activating one or more electronic devices when the medical personnel enters a patient room; obtaining image data acquired by the one or more electronic devices that captures the medical personnel; analyzing the acquired image data to identify the medical personnel and at least one medical apparatus to be used by the medical personnel for the procedure; analyzing the acquired image data to monitor the medical personnel's performance of the procedure using the at least one identified medical apparatus; and storing data acquired from the monitored performance of the procedure in a database.

Figure 1:
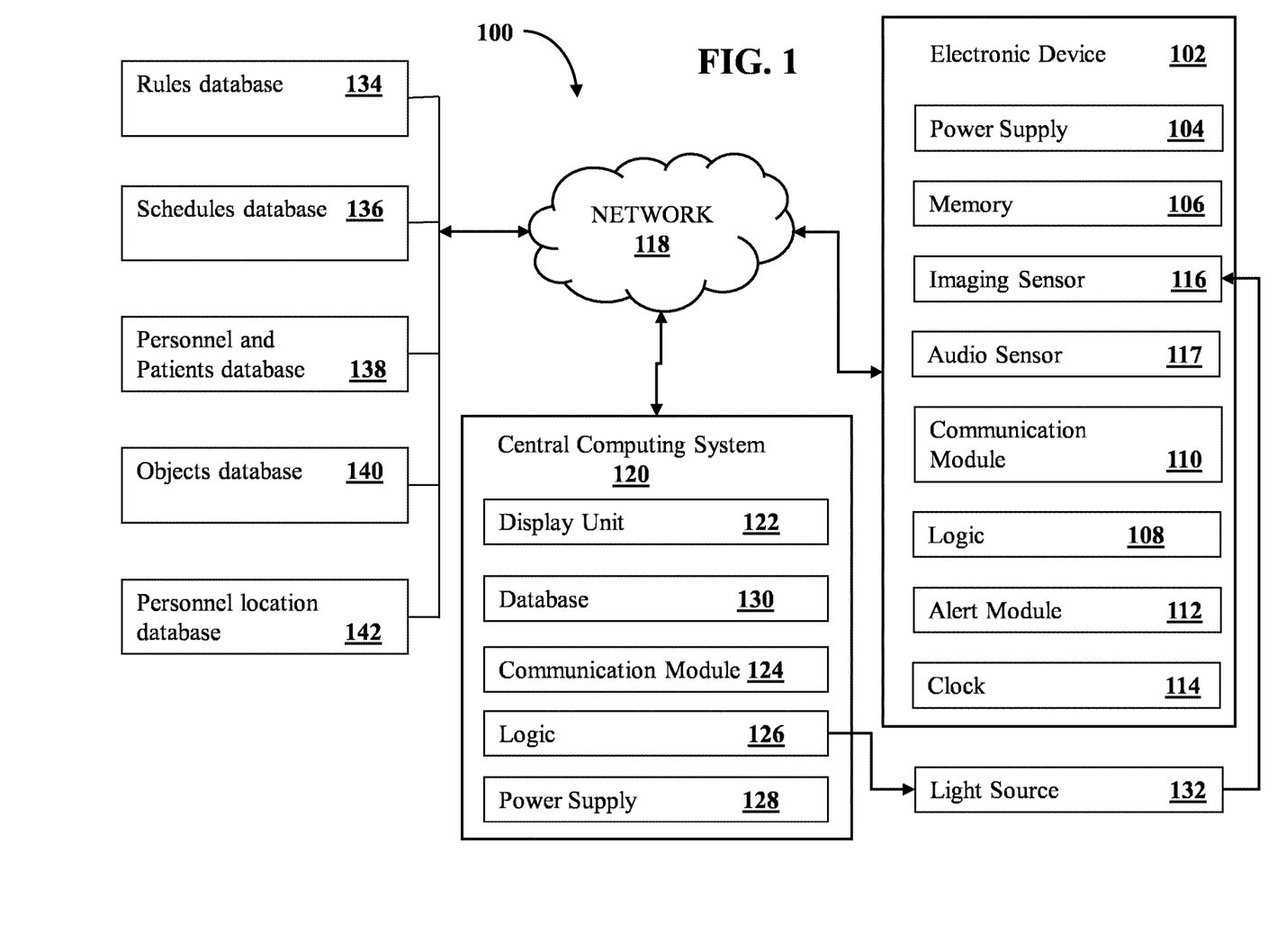
FIG. 1 illustrates a system for detecting, identifying, and monitoring a medical personnel performing a procedure, according to various embodiments of the present disclosure.

FIG. 1 illustrates a system according to one embodiment of the present disclosure for identifying, locating, and monitoring a procedure performed by a medical personnel. As shown, a system 100 comprises one or more electronic devices 102 and a central computing system 120. Each electronic device 102 may include one or more of a power supply 104, a memory 106, logic 108, a communications module 110, an alert module 112, a clock 114, an imaging sensor 116, an input to acquire image data from one or more imaging sensors (for example, cameras) 116, and/or an audio sensor 117. The one or more electronic devices 102 may communicate with each other and/or with the central computing system 120 via a network 118. The central computing system 120 may include various standard computing components, such as a display unit 122, a communications module 124, logic 126, a power supply 128, and/or a database 130. In various embodiments, the central computing system's logic 126 may be capable of activating and/or controlling light emitted by one or more light sources 132, as will be described below. The one or more electronic devices 102 may also be connected via the network 118 to a rules database 134, a schedules database 136, personnel and patients database 138, an objects database 140, and/or a personnel location database 142.

Logic 108 and 126 may come in various forms. In some embodiments, logic 108/126 may take the form of one or more processors, and memory 106 of electronic device 102 or memory (not depicted) of central computing system 120 may store instructions that may be executed by the one or more processors to perform various techniques described herein. In some embodiments, logic 108/126 may take the form of an application-specific integrated circuit ("ASIC") or a field-programmable gate array ("FPGA"). Memory 106 may come in various forms as well, including but not limited to high-speed random access memory or non-volatile memory such as magnetic disk storage devices, optical storage devices, and flash memory.

Imaging sensor 116 may come in various forms in various embodiments. These types are well-known and are available commercially. Commonly used image sensors are semiconductor charged-coupled devices ("CCD") or active pixel sensors in complementary metal-oxide-semiconductor ("CMOS"). Examples of imaging sensors may include digital cameras, video cameras, CCTVs, webcams and smart cameras.

Various types of audio sensors 117 may be employed as well, most of which are well-known and are available commercially. Many of these sound sensors are microphone-based. Examples of microphone-based sound sensors are piezoelectric microphones, MEMS microphones, condenser microphones, fiber optic microphones, electret condenser microphones, dynamic microphones, ribbon microphones, carbon microphones, laser microphones, and liquid microphones.

The communications modules 110 and 124 may be stand-alone devices or components of devices that facilitate communication, e.g., sending and receiving of commands, triggers, notifications, prompts, acknowledgments, information, messages, forms, and various types of data such as video, text, and audio between, for example, the one or more electronic devices 102 and central computing system 120. In accordance with various embodiments, communications modules 110 and 124 may include any transmitter or receiver used for Wi-Fi, Bluetooth, infrared, NFC, radio frequency, cellular communication, visible light communication, Li-Fi, WiMax, ZigBee, fiber optic and other forms of wireless communication devices. Alternatively, the communications module 110 and/or 124 may be physical channels such as USB cables. Ethernet cables, or other wired forms of communication.

In various embodiments, objects database 140 may store image data portraying medical devices, equipment, medical supplies, nonmedical devices, medical apparel, and/or other objects found in a medical setting or a patient room. Personnel and patients database 138 may store medical personnel and patient information, including their photos, recorded voice data, and in some cases, video data. Personnel location database 142 may store one or more of last known locations of medical personnel and records of past locations of medical personnel. In some embodiments, personnel location database 142 may be incorporated as part of personnel and patients database 138.

Rules database 134 may store data and pre-stored parameters corresponding to one or more rules for performing a medical procedure. For example, rules database 134 may store appropriate amounts of time for which particular actions should be performed (e.g., a doctor should scrub his or her hands for two minutes prior to performing some evaluation), expected order of operations for various medical procedures, expected operational parameters of medical equipment, etc. Rules database 134 may also store corresponding decisions and actions resulting from a comparison of those pre-stored data and parameters with detected, monitored, or measured one or more data and parameters.

Schedules database 136 may store information, data, and pre-stored parameters corresponding to the schedules of one or more actions, events, tasks, and medical procedures to be performed by a medical personnel. Examples of medical procedures include, but are not limited to, checking the vital signs of a patient, administering intravenous fluid levels, checking hospital equipment status, administering medicines, performing physical therapy, monitoring the intake of those medicines, performing or assisting in performing patient baths, taking X-rays, taking blood samples, and so forth.

Figure 2:
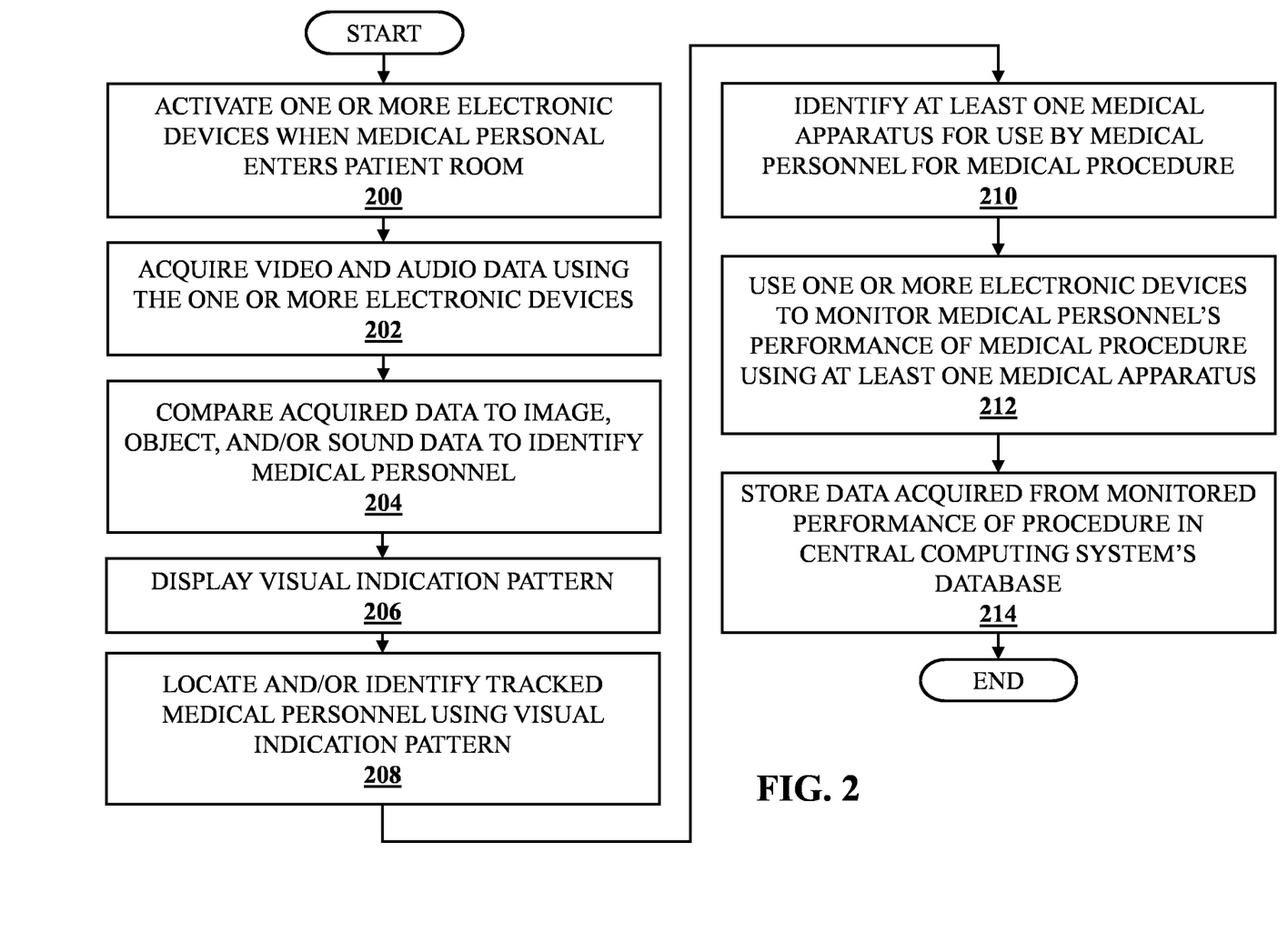
FIG. 2 illustrates a method for monitoring a procedure performed by a medical personnel according to various embodiments of the present disclosure.

FIG. 2 illustrates an example method for monitoring a procedure performed by a medical personnel. When a medical personnel enters a patient room, at block 200, one or more electronic devices (e.g., 102 in FIG. 1) may be activated either automatically or manually. For example, the medical personnel may actuate a switch or other similar mechanism when he or she enters the room that causes the one or more electronic devices to activate. As another example, a motion sensor may detect that someone has entered the room and activate the one or more electronic devices in response. As yet another example, an radio frequency identification ("RFID") reader may read an RFID signal emitted by a badge or other mechanism worn or carried by medical personnel, and may activate the one or more electronic devices in response. In various embodiments, "activating" an electronic device may cause the device to, among other things, begin acquiring image and/or audio data.

At block 202, the one or more electronic devices may then acquire image and/or audio data. At block 204, the acquired image and/or audio data may be compared, e.g., by the one or more electronic devices, with the image data, object data, and sound data stored in the objects database (e.g., 140 in FIG. 1) and personnel and patients database (e.g., 138 in FIG. 1) to determine the identity of the medical personnel who entered the patient room to perform a medical procedure. For example, image data captured by imaging sensor 116 may be analyzed using various image processing techniques to identify medical personal and/or indicia worn by medical personnel. In some embodiments, facial recognition may be employed to identify the medical personnel. In some embodiments, visual indicia such as bar codes or quick response ("QR") codes adorned by medical personnel may be recognized. In some embodiments, audio data captured by audio sensor 117 may additionally or alternatively be analyzed, e.g., using voice recognition, to identify medical personnel or confirm an initial identification made using image data captured by imaging sensor 116.

Once the medical personnel is identified, at block 206, the system may automatically activate and display a visual identification pattern, for example, blinking or flashing of LEDs located in front of the patient rooms in a preprogrammed sequence and color combination uniquely assigned to each medical personnel. At block 208, one or more cameras in the hallway, for example, may then locate and correctly identify the medical personnel being tracked using the preprogrammed visual identification pattern.

During the performance of the medical procedure, the medical personnel may use an at least one medical apparatus—e.g., an infusion pump, defibrillator, catheter, injection pen, or a dialysis machine, etc. At block 210, this medical apparatus may be detected and identified by analyzing image and/or audio data acquired by the one or more electronic devices at block 202. Similarly, medical supplies (e.g., disinfectants, absorbent pads, gloves, conductive gel, IV fluid, medicines, and dressing aids) and medical apparel (e.g., radiation protective suits and surgical masks) may be detected and identified at block 210.

As the medical personnel performs the medical procedure while wearing the medical apparel and/or while using the at least one medical apparatus and/or medical supplies, at block 212, the one or more electronic devices may monitor the medical personnel's performance to assure strict compliance with medical standard operating protocols stored in the rules database (e.g., 134 in FIG. 1). For example, by analyzing image and/or audio data acquired by one or more electronic devices, it may be determined whether the medical personnel operated the at least one medical apparatus for an appropriate amount of time. As another example, it may be determined whether the medical personnel wore appropriate medical apparel and/or wore it for a sufficient amount of time. If a doctor wears medical gloves for part of a procedure, but then discards them before completing the procedure, the doctor may have violated one or more protocols in the rules database (e.g., 134 in FIG. 1).

At block 214, data acquired from the monitored performance of the procedure may then be stored, e.g., in the central computing system's database (e.g., 130 in FIG. 1). In some embodiments, if it is determined that the medical personnel did not comply with the medical standard operating protocols, the one or more electronic devices may send an alert to the hospital's central computing system to notify other medical personnel.

The flashing of the colored lights (e.g., 132 in FIG. 1) according to a specific pattern is used to indicate identity of the medical personnel, e.g., to nearby electronic devices such as hallway cameras. In some embodiments, different color LEDs may be used. The LEDs may be programmed to blink or flash according to a specific sequence and color combination unique to each medical personnel. Thus, not only will the system of the present disclosure be able to determine the presence of a medical personnel in a hospital room, but it will also be able to determine the medical personnel's identity. For example, one doctor may have an identifying LED flashing pattern comprising one blue LED followed by two consecutive red LEDs, or a nurse may have an identifying LED flashing pattern comprising one red LED followed by one blue LED. In some embodiments, one or more infrared light sources may be used to generate the uniquely-assigned visual identification pattern to be detected by one or more imaging devices. For detecting the infrared light patterns, one or more infrared cameras may be used as the imaging devices. A major advantage of infrared light sources is they are imperceptible to humans, which prevents any visual distraction or discomfort that may be caused by constantly blinking visible lights. In some embodiments, two or more infrared light sources may be used to generate the visual identification pattern. For example, an attending physician may be assigned an identification pattern wherein the first infrared light source blinks once followed by a second infrared light source blinking twice. As another example, a nurse may be assigned an identification pattern wherein the first infrared light source blinks three times and the third light source blinks twice. In some embodiments, the infrared light sources also may be used for heating the hospital hallways.

In one aspect of the present disclosure, the programmable LED blinking patterns may be implemented in conjunction with an identification system such as a biometric sensor or password authentication system. The biometric identification system may be based on iris, retina, palm, fingerprint, voice, facial, or any combination of these features. The password authentication system may be based on password entry using either physical or touch buttons. Upon authentication of the medical personnel, the system will automatically display the corresponding LED flashing pattern uniquely assigned to the medical personnel using the LED lights located in front of the patient rooms. Electronic devices such as cameras may then be able to determine the location and identity of the medical personnel being tracked from the detected flashing LED patterns.

The purpose of the medical personnel's patient room visitation can also be indicated by a unique LED flashing pattern. For example, a routine patient visitation by an attending physician in a certain patient room may be indicated by one blue LED followed by two consecutive red LEDs, which identifies the physician, followed after a short time interval, by three successive green LEDs that indicate that the physician is merely conducting a scheduled hospital round inside the patient room. Similarly, the LED identification system may have alternately blue and red flashing LEDs to indicate that a nurse is currently administering medicines and performing vital signs check-up on the patient inside the patient room. In some embodiments, a unique LED flashing pattern may be initiated to signal that a scheduled patient procedure has not been performed in a particular patient room after a predefined time has passed for the scheduled procedure.

In another embodiment of the present disclosure, two imaging devices may be installed at both ends of a hospital hallway to detect and identify medical personnel going in and out of the patient rooms. One of the two imaging devices may detect and identify, e.g., via a facial or retinal recognition algorithm, a doctor walking towards a particular room. That imaging device may then transmit the identity and location of the doctor to the hospital's central computing system (e.g., 120 in FIG. 1). The central computing system may then activate the identification lighting system (e.g., 132 in FIG. 1) in front of the particular room and trigger the flashing of the assigned visual identification pattern for the doctor. When a nurse needs to determine the doctor's location in the hospital premises, the nurse or security guard only needs to use the hospital's imaging system to determine the doctor's location by searching for the location of the matching visual identification pattern generated by the assigned two or more infrared LEDs. Once detected and identified, the imaging device transmits the location to the hospital's imaging system. In this embodiment, the visual identification pattern may be continuously generated by the two or more infrared LEDs until it is determined by one or more electronic devices that the doctor had exited the particular room.

Figure 3:
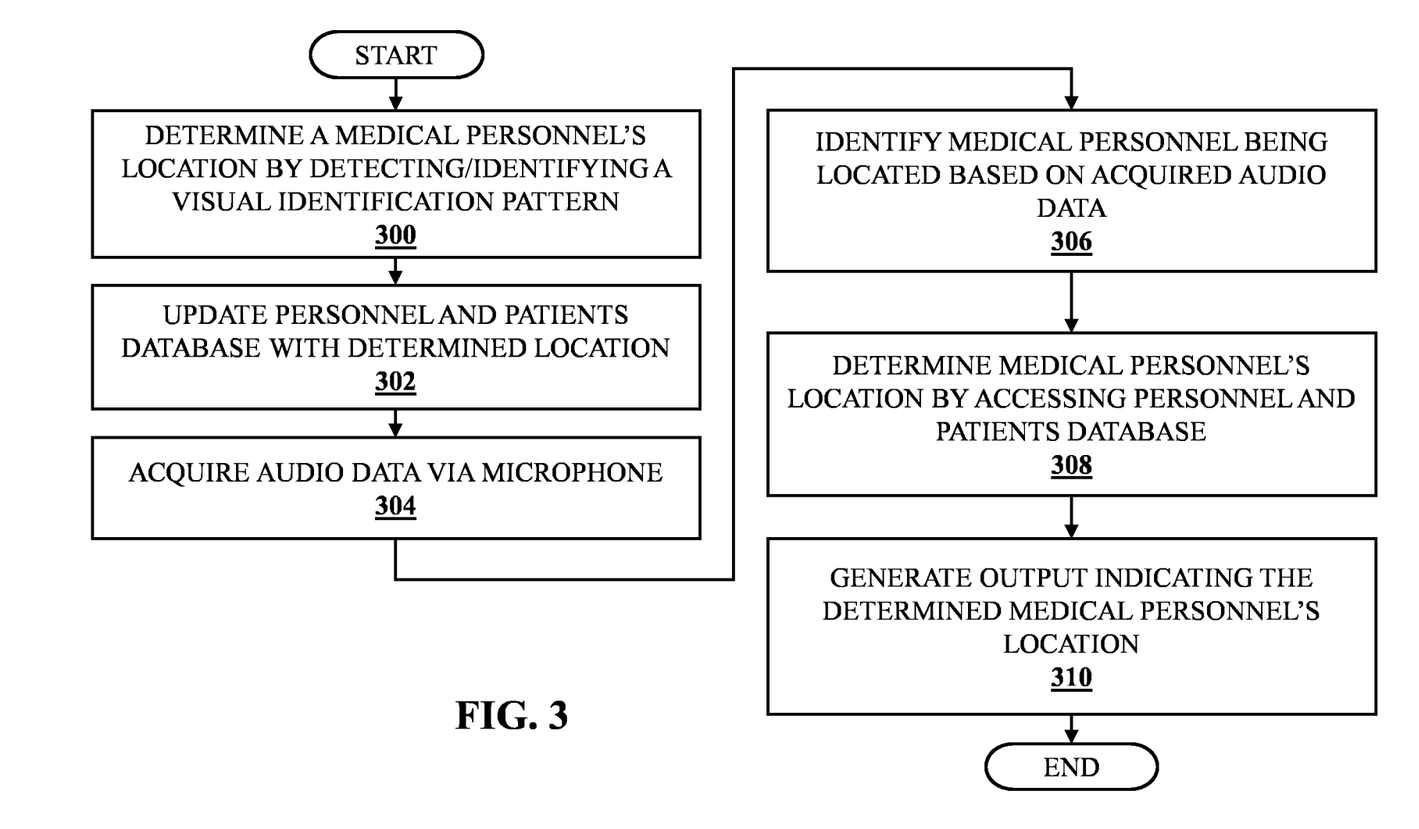
FIG. 3 illustrates a method for determining a medical personnel's location by using an audio-based identification system.

In another embodiment of the present disclosure, an audio-based personnel identification system ("APIS") may be used to respond to a query about a medical personnel's location. The APIS may include, for instance, a microphone (e.g., audio sensor 117 in FIG. 1) for acquiring audio data from a medical personnel, one or more processors for executing a speech-to-text algorithm to determine the medical personnel being located based on the acquired audio data, and an APIS speaker for generating an audio output in response to the query. Referring to FIG. 3, at block 300, the APIS may determine one or more medical personnel's location by detecting and identifying the visual identification patterns generated by one or more light sources in front of each patient room.

In various embodiments, the medical personnel's identity may be determined from the visual indication pattern itself (e.g., information modulated into the visual indication pattern). The medical personnel's location may be determined from additional information modulated into the visual indication pattern, from one or more attributes of the light sources (e.g., LEDs) that emitted the visual indication pattern, and/or from one or more attributes of the imaging device (e.g., 116 in FIG. 1) that captured the visual indication pattern. For instance, a particular camera may have a location that is known, and/or may be known to be pointed at one or more light sources that are known to be at a particular location. The medical personnel's location may therefore be inferred from the known location of the camera and/or the captured light sources. Additionally or alternatively, the light sources may emit, e.g., interspersed with the visual indication pattern that identifies the medical personnel or at a different wavelength, an additional visual indication pattern that identifies a location. However the medical personnel's location is determined, at block 302, the personnel and patients database (e.g., 138 in FIG. 1) and/or personnel location database (e.g., 142 in FIG. 1) may be updated by storing the determined one or more medical personnel's location.

At block 304, a microphone may acquire audio data comprising a spoken request for a location of one medical personnel by another medical personnel. For example, a nurse may say, "Please locate Doctor Johnson." Based on the audio data acquired at block 304, at block 306 the sought-after medical personnel may then be identified via speech recognition. For example, standard speech recognition techniques such as hidden Markov models, dynamic time warping, neural networks, and so forth, may be employed to extract, from the acquired audio data, an identifier (e.g., name, employee number, etc.) of the sought-after medical personnel. In some embodiments, a grammar may be generated and maintained for the names of all medical personnel currently employed at the facility, e.g., to aid in recognizing their names when spoken.

At block 308, the APIS may determine the searched-for medical personnel's location by accessing the personnel and patients database (e.g., 138 in FIG. 1) and/or the personnel location database (e.g., 142 in FIG. 1). At block 310, the APIS may activate a speaker to generate an audio output indicating the medical personnel's location. For example, suppose nurse A attempts to locate physician A by saying (at block 304) "Where can I find physician A?" to a microphone located in front of patient room A. To determine the physician A's location, the APIS may access (at block 308) the personnel and patients database and/or personnel location database to determine that physician A is in patient room B. The APIS may then activate the speaker located in front of patient room A to inform nurse A (at block 310) that physician A is currently in patient room B.

As another example, suppose a nurse working at a nursing station needs to locate Dr. John Doe in the hospital premises. After being authenticated by APIS, the nurse queries APIS and asks "APIS, where is Dr. John Doe right now?" APIS then searches the personal and patients database (e.g., 138 in FIG. 1) and/or the personnel location database (e.g., 142 in FIG. 1) to retrieve the most recent stored location of Dr. John Doe. After determining that Dr. John Doe is in room 206, APIS then relays the doctor's location to the nursing station and issues an audio response to the nursing station "Dr. John Doe is in room 206 right now." The nurse then requests APIS to open a direct audio channel to room 206 by issuing the request "APIS, please open an audio channel to room 206." Alternatively, the nurse requests APIS to open an audio-visual channel to room 206 to allow direct communication with Dr. John Doe via video and audio channels.

Figure 4:
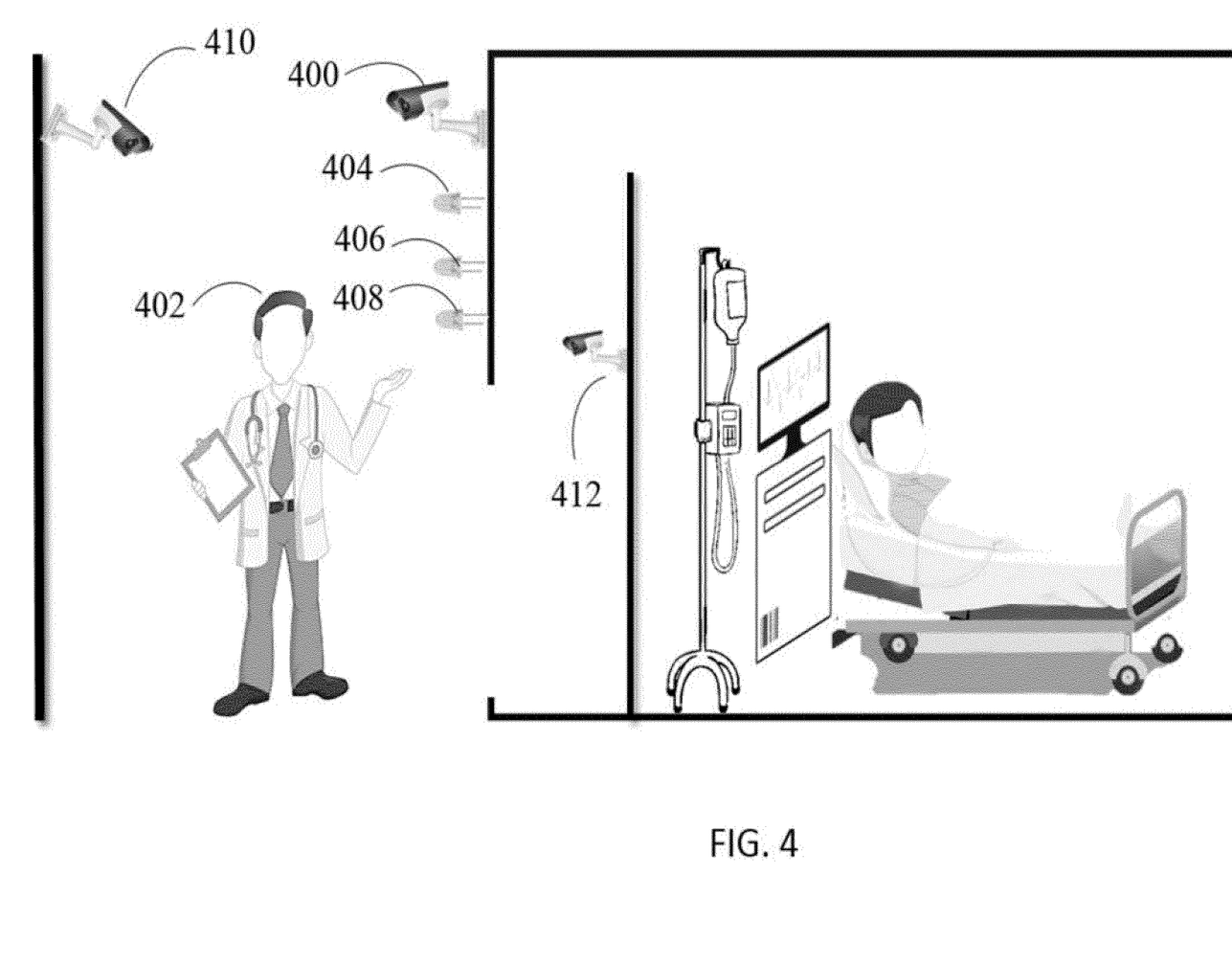
FIG. 4 illustrates an example system for determining a medical personnel's identity by identifying and detecting a visual identification pattern generated by infrared light sources.

In an example embodiment illustrated in FIG. 4, a first imaging device 400 mounted adjacent an entrance to a patient's room may acquire image data of a surgeon 402 outside the patient's room, e.g., in a hallway. By employing facial recognition or other image processing techniques on the acquired image data, the surgeon 402 may be identified e.g., by circuitry internal to the imaging device 400 or by another device (e.g., central computing system 120 in FIG. 1) to which imaging device 400 is associated.

When the surgeon 402 is detected entering a preparation and/or operating room, a trigger may be initiated to unlock the door and activate three infrared LEDs, 404, 406, and 408. The three infrared LEDs 404-408 may emit a variety of blinking patterns that are assigned to various medical personal. For example, the infrared LED 404 may blink twice, and then infrared LED 406 may blink once followed by the infrared LED 408 blinking twice, which may correspond to the blinking pattern assigned to the surgeon 402. In some embodiments, the blinking pattern of the infrared LEDs (404, 406, and 408) may be repeated for a preset time interval, e.g., every five minutes. A second imaging device 410 located in the hallway may then acquire image data (also referred to as "location image data") that captures the blinking pattern emitted by the infrared LEDs (404, 406, and 408). Based on the captured blinking pattern or on a known location of the LEDs 404-408, it may be determined, e.g., by circuitry internal to the second imaging device 410 or by another electronic device (e.g., 120 in FIG. 1), that the surgeon 402 is inside the patient room. The surgeon's location may then be transmitted to and stored in the personnel location database (e.g., 142 in FIG. 1).

While the surgeon 402 is inside the preparation room, a third imaging device 412 may be configured to acquire visual and/or audio data for a predetermined time interval (e.g., ten minutes) from the surgeon's entry into the preparation room. Based on the acquired data, it may be determined whether the surgeon has complied with a scrubbing protocol contained in the rules database (e.g., 134 in FIG. 1). Scrubbing protocols may require surgeons to scrub their hands and arms upon (or prior to) entering the operating room, the required scrubbing being typically done for a minimum of at least three minutes. When it is determined based on data acquired by the third imaging device 412 that the surgeon 402 scrubbed his hands and arms for only two minutes, the APIS may notify the surgeon, e.g., with audio and/or visual output, of the potential breach in protocol.

Figure 5:
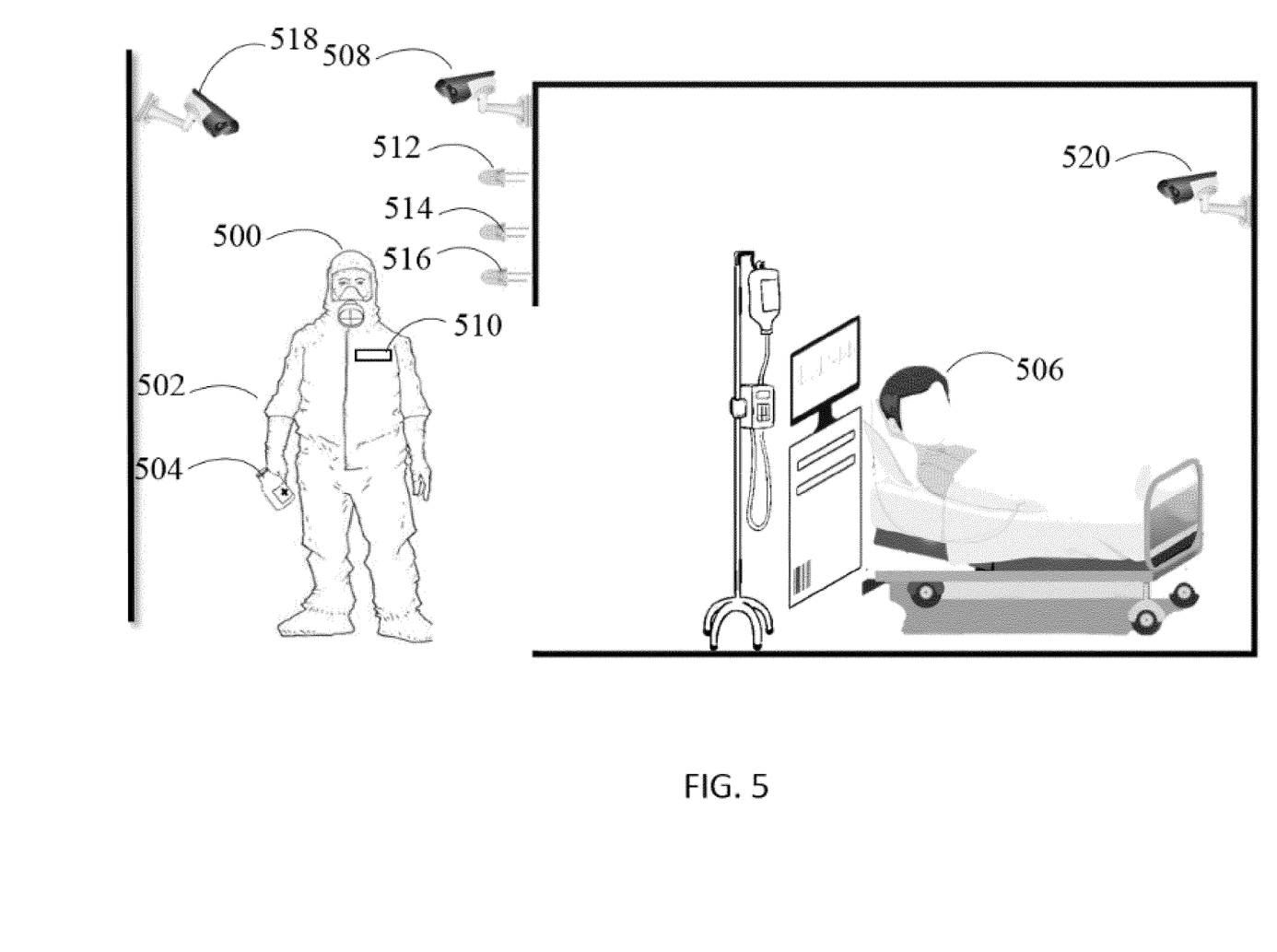
FIG. 5 illustrates an example of a system for detecting, identifying, and monitoring a medical personnel performing a procedure according to one embodiment of the present disclosure.

In another embodiment illustrated in FIG. 5, suppose an oncologist 500 wearing a radiation protective suit 502 is scheduled to administer radioactive iodine 504 (e.g., in capsule form) to a patient 506 undergoing systemic radiation therapy due to thyroid cancer. Before or while the oncologist 500 enters the patient room, a first imaging device 508 located in front of the patient room may detect an infrared LED tag 510 attached on the oncologist's radiation protective suit 502. A flashing pattern emitted by the infrared LED tag 510 may be captured in image data acquired by the first imaging device 508. By analyzing the captured image data, the infrared LED tag's flashing pattern may be detected and used to determine the oncologist's identity. The system may then trigger one or more LEDs, such as the three infrared LEDs, 512, 514, and 516 located in front of the patient room in FIG. 5, to emit a particular pattern. In some embodiments, the three LEDs 512, 514, and 516 may emit the same flashing pattern emitted by the infrared LED tag 510. The flashing pattern emitted by the three LEDs 512, 514, and 516 may be captured in image data acquired by a second imaging device 518 located in the hallway. Image data acquired by the second imaging device 518 may then be analyzed to detect and/or determine that the oncologist 500 is inside the patient room.

Thereafter, schedule data may be retrieved from the schedules database (e.g., 136 in FIG. 1) to determine if a scheduled medical procedure is to be performed by the oncologist 500. Based on the retrieved schedule data, it may be determined, e.g., by circuitry internal to the first imaging device 508 or by another computing device (e.g., 120 in FIG. 1), that radioactive iodine 504 is scheduled to be administered to the patient 506. Image data acquired by the first imaging device 508 may then be analyzed (e.g., by circuitry internal to first imaging device 508 or by another electronic device) to detect and verify if the oncologist 500 is wearing a proper radiation protective suit 502. For example, an image of the oncologist 500 may be captured by first imaging device 508 and compared with a previously stored image of a radiation protective suit, e.g., in the objects database 140.

Once the oncologist 500 is verified to be wearing a proper radiation protective suit, the patient room's door may be unlocked, e.g., by circuitry internal to first imaging device 508 or by another electronic component. The oncologist 500 may then enter the patient room and provide the patient with the radioactive iodine 504 and a glass of water. A third imaging device 520 located inside the patient room may acquire image data of the oncologist 500 during the administration of radioactive iodine 504. This image data may be analyzed to verify whether the oncologist 500 is administering (or did administer) the correct drug (i.e., radioactive iodine 504) and dosage. For example, the image data acquired by third imaging device 520 may be analyzed to detect and/or identify a barcode printed on the radioactive iodine's bottle 504. After verifying that the correct drug is administered to the patient 506, a notification may be sent, e.g. by third imaging device 520 or by another electronic device, to the hospital's central computing system (e.g., 120 in FIG. 1) to indicate the completion of the scheduled medical procedure to the patient 506.

Figure 6:
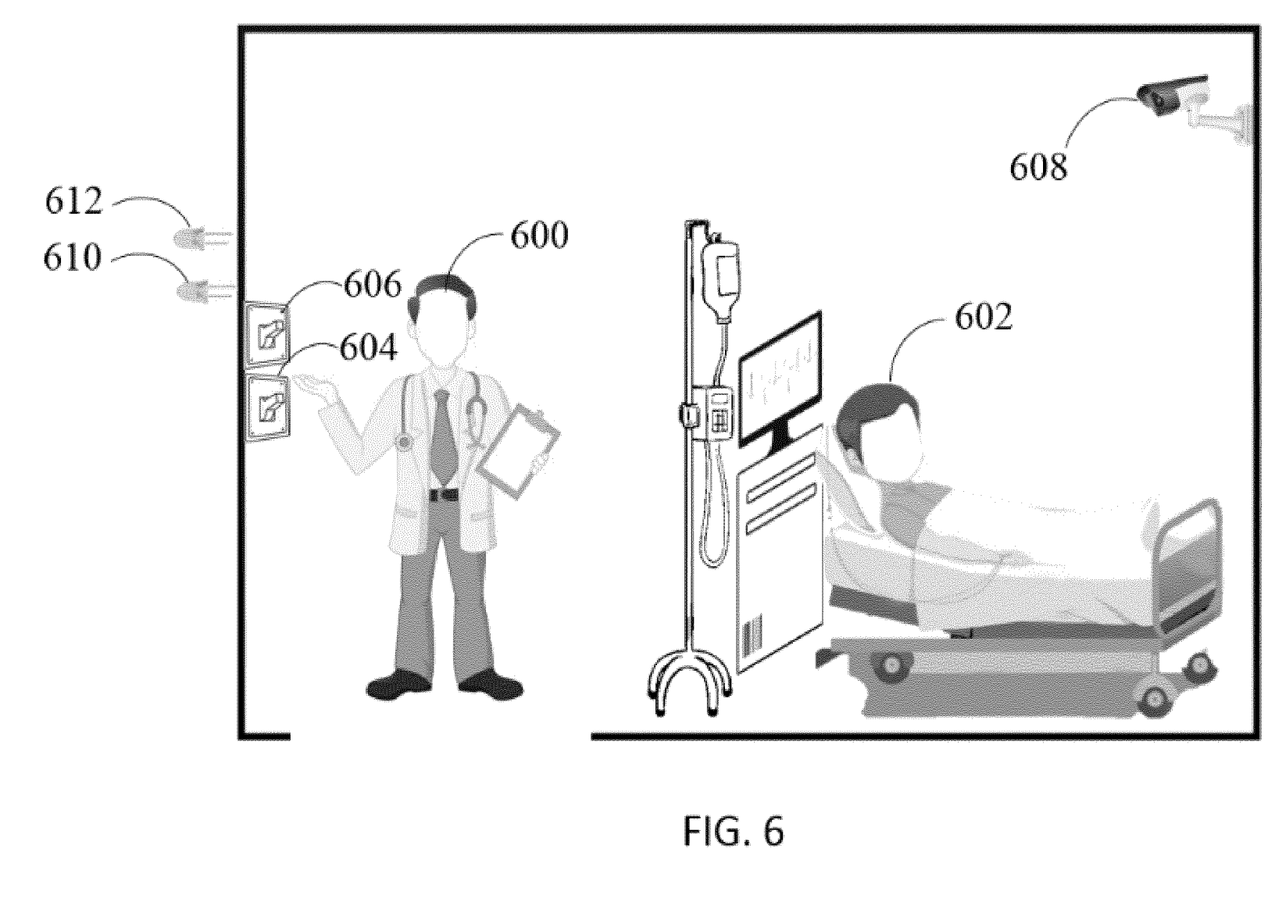
FIG. 6 illustrates an example of a system for detecting, identifying, and monitoring a medical personnel performing a procedure according to one embodiment of the present disclosure.

Another example is depicted in FIG. 6. Suppose a medical personnel 600 performing patient rounding is scheduled to administer Azithromycin (i.e., an antibiotic for treating bacterial infections of patients initially diagnosed with community-acquired and mild pneumonia) intravenously to a patient 602 initially diagnosed of having pneumonia. Suppose further that the medical personnel 600 enters the patient room and actuates a switch 604. Here, each switch may correspond to an identity of one or more medical personnel. For example, switch 604 may correspond to a nurse and switch 606 may correspond to a physician.

When the medical personnel 600 enters the patient room, the camera 608 located in the patient room may acquire image data that portrays the light switch 604 being actuated by the medical personnel 600. Analysis of the acquired image data may reveal that switch 604 was actuated, and therefore, medical personnel 600 is a nurse. The identification of the medical personnel's role may be performed, for instance, by comparing the actuated light switch 604 image with a previously stored light switch image in the objects database. When it is determined based on image data captured by the camera 608 that a nurse 600 is inside the patient room, the green LED 610 located in front of the patient room may be activated, e.g., by circuitry internal to the camera 608 or by another computing device (e.g., 120 in FIG. 1), to indicate the nurse's presence inside the patient room.

Thereafter, schedule data, e.g., from schedules database 136, may be received and examined to determine if a scheduled medical procedure is supposed to be performed on the patient by the nurse 600. Suppose that, in this example, it is determined based on the retrieved schedule data that Azithromycin must be administered intravenously and slowly for an hour to the patient 602 as prescribed by an attending physician. The camera 608 may capture image and/or data of the nurse 600 while the nurse injects the Azithromycin. This image and/or audio data may be analyzed to verify that the nurse 600 is administering the correct drug (i.e., Azithromycin), drug concentration, and dosage, e.g., by detecting and identifying an image pattern printed on the Azithromycin container. In some embodiments, the unique pattern or set of symbols may be unique to each medical supply or apparatus. In another embodiment, optical character recognition may be used on image data acquired by the camera 608 to analyze written text for accurate identification of the medical supply and apparatus. When it is verified that the correct drug has been properly administered to the patient 602, a notification may be sent to the hospital's central computing system (e.g., 120 in FIG. 1) to indicate the completion of the scheduled medical procedure to the patient 602.

In some embodiments of the present disclosure, voice recognition may be used to identify a medical personnel via a microphone (e.g., audio sensor 117 in FIG. 1) placed in front of the patient room, in addition to or instead of image data as was used in FIGS. 4-6. The medical personnel may attempt to enter the patient room by speaking "The doctor is in" into the microphone. The medical personnel may then be recognized via voice recognition that triggers the unlocking of the patient room's door and the activation of one or more LEDs (e.g., a red LED, a blue LED, and a green LED) located in front of the patient's room. The one or more of LEDs may emit light in various blinking patterns in a manner that can be detected by an imaging device (e.g., 116 in FIG. 1) located in the hallway. For example, in one embodiment, one of the LEDs, such as the green LED, may blink a number of times (e.g., thrice) followed by the blue LED blinking any number of times. Such a blinking pattern may be repeated every so often, e.g., every five minutes, until disabled by the automated monitoring system. The hallway imaging device may acquire image data that portrays the blinking pattern of the LEDs in front of the patient room. This imaging data may be analyzed to determine that the medical personnel is inside the operating room.

In another aspect of the present disclosure, LEDs located in front of a patient room may also function as visual alerts for medical personnel. When a patient monitoring system detects that the patient's vital signs are not within the normal threshold level (e.g., patient's heart rate is 30 bpm), a red LED may blink, e.g., every half second, to notify any medical personnel passing the hallway in front of the patient room. The red LED may continuously blink every half a second until a medical personnel recognized based on image and/or audio data captured outside the patient's room enters the patient's room. In this case, rather than a sound alarm, a visual alarm is used to allow a medical personnel to immediately respond to the patient in critical condition.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The present disclosure is not intended to be restricted to the several exemplary embodiments of the disclosure described above. Other variations that may be envisioned by those skilled in the art are intended to fall within the disclosure.

The invention claimed is:

1. A method for monitoring compliance with medical procedures comprising:
   receiving, via at least one of a reader or a sensor, activation data when a medical personnel enters a patient room;
   activating, by one or more processors, one or more electronic devices based on the activation data, wherein the activating triggers the one or more electronic devices to begin acquiring image data in the patient room, wherein the acquired image data includes data capturing the medical personnel;
   analyzing, by applying image detection algorithms via the one or more processors, the acquired image data to identify the medical personnel and at least one medical apparatus to be used by the medical personnel to perform a procedure, wherein the analyzing to identify the medical personnel and at least one medical apparatus comprises comparing the acquired image data to at least one of image data or object data stored in an objects database and/or a personnel and patients database;
   analyzing, by applying image detection algorithms via the one or more processors, the acquired image data to monitor the medical personnel performing the procedure using the at least one identified medical apparatus to determine compliance with a protocol, wherein the analyzing to determine compliance comprises comparing at least one aspect of the acquired image data to medical standard operating protocols stored in a rules database; and
   storing, by the one or more processors, data acquired from the monitored performance of the procedure in a compliance database.

2. The method of claim 1, further comprising:
   activating and displaying a visual identification pattern uniquely assigned to the medical personnel when the medical personnel has been identified.

3. The method of claim 2, wherein the visual identification pattern is generated by one or more infrared light sources.

4. The method of claim 2, wherein the visual identification pattern comprises printed indicia adorned by the medical personnel.

5. The method of claim 1, further comprising:
generating and rendering, by the one or more processors using a speaker, audio output that notifies the medical personnel of non-compliance with the medical standard operating protocols.

6. The method of claim 1, further comprising:
obtaining, by the one or more processors, audio data acquired by the one or more electronic devices; and
analyzing, by the one or more processors, the acquired audio data to further identify the medical personnel.

7. The method of claim 1, further comprising:
causing, by the one or more processors, one or more light sources to emit a visual indication pattern that is associated with the identified medical personal.

8. The method of claim 7, further comprising:
obtaining, by the one or more processors, location image data acquired by the one or more electronic devices that captures the one or more light sources emitting the visual indication pattern;
determining, by the one or more processors based on the location image data or a known location associated with the one or more light sources, a location of the medical personnel; and
causing, by the one or more processors, the determined location to be stored in a personnel location database.

9. The method of claim 8, further comprising:
obtaining, by the one or more processors, audio data acquired by the one or more electronic devices that captures a spoken request for a location of a sought-after medical personnel;
analyzing, by the one or more processors using speech recognition, the audio data to identify the sought-after medical personnel;
determining, by the one or more processors based on data stored in the personnel location database, a last known location of the sought-after medical personnel; and
generating, by the one or more processors, audio output that includes an indication of the last known location of the sought-after medical personnel.

10. A system for tracking a location of a medical personnel comprising:
at least one of a reader or a sensor to provide activation data when the medical personnel enters a patient room;
one or more processors programmed to execute logic to activate, based on the activation data, one or more electronic devices, wherein the activation triggers the one or more electronic devices to begin acquiring image data in the patient room, wherein the acquired image data includes data capturing the medical personnel;
one or more light sources placed adjacent the patient room to generate a visual identification pattern assigned to the medical personnel on determination that the medical personnel has entered the patient room;
an input to acquire, from the one or more electronic devices, image data that captures the visual identification pattern; and
a personnel location database for storing a record of a location of the medical personal,
wherein the one or more processors are further programmed to execute logic to analyze the acquired image data, using image detection algorithms, to determine an identity of the medical personnel and at least one medical apparatus to be used by the medical personnel to perform a procedure based on the captured visual identification pattern by comparing the acquired image data to at least one of image data or object data stored in an objects database and/or a personnel and patients database; and
wherein the one or more processors are further programmed to execute logic to monitor the medical personnel performing the procedure using the at least one identified medical apparatus to determine compliance with a protocol by comparing at least one aspect of the acquired image data to medical standard operating protocols stored in a rules database.

11. The system of claim 10, wherein the logic to analyze the acquired image data determines the location of the medical personnel based on one or attributes of the one or more electronic devices that acquired the image data.

12. The system of claim 10, wherein the logic to analyze the acquired image data determines the location of the medical personnel based on a known location of the one or more light sources.

13. The system of claim 10, wherein the logic to analyze the acquired image data determines the location of the medical personnel based on information modulated into the visual identification pattern.

14. The method of claim 1, wherein the analyzing to identify comprises performing facial recognition of the medical personnel.

15. The method of claim 1, wherein the analyzing to identify comprises identifying bar codes or quick response (QR) codes adorned by the medical personnel.

16. The method of claim 2, wherein the visual identification pattern comprises blinking or flashing LEDs located in front of the patient room in a preprogrammed sequence and/or color combination.

17. A system for tracking a location of a medical personnel comprising:
at least one of a reader or a sensor configured to provide activation data when the medical personnel enters a patient room;
one or more electronic devices configured to acquire image data in the patient room;
one or more processors coupled to the at least one of the reader or the sensor and the one or more electronic devices; and
one or more non-transitory memories that store instructions that, when executed by the one or more processors, cause the one or more processors to:
activate the one or more electronic devices based on the activation data provided by the at least one of the reader or the sensor, wherein the activating triggers the one or more electronic devices to begin acquiring image data in the patient room, wherein the acquired image data includes data capturing the medical personnel;
analyze the acquired image data to identify the medical personnel and a medical apparatus in the patient room to be used by the medical personnel to perform a procedure, wherein the analyzing to identify the medical personnel and the medical apparatus comprises comparing the acquired image data to at least one of image data or object data stored in an objects database and/or a personnel and patients database;
analyze the acquired image data to monitor the medical personnel performing the procedure using the medical apparatus to determine compliance with a protocol, wherein the analyzing to determine compliance comprises comparing at least one aspect of the acquired image data to medical standard operating protocols stored in a rules database; and store data acquired from the monitored performance of the procedure in a compliance database.

18. The system of claim 17, wherein the instructions further cause the one or more processors to:

activate and display a visual identification pattern uniquely assigned to the medical personnel when the medical personnel has been identified.

19. The system of claim 18, wherein the visual identification pattern is generated by one or more infrared light sources.

20. The system of claim 18, wherein the visual identification pattern comprises blinking or flashing LEDs located in front of the patient room in a preprogrammed sequence and/or color combination.

\* \* \* \* \*